(12) United States Patent
Sabapathy (10) Patent No.: US 7,459,282 B2
(45) Date of Patent: Dec. 2, 2008

(54) USE OF C-JUN OR C-JUN ACTIVATING AGENTS SUCH AS UV OR C-JUN N-TERMINAL KINASES (JNKS) FOR TREATING CANCER

(75) Inventor: Kanaga Sabapathy, Singapore (SG)

(73) Assignee: Biotech Research Ventures Pte Limited, Singapore (SG)

( * ) Notice: Subject to any disclaimer, the term of this patent is extended or adjusted under 35 U.S.C. 154(b) by 330 days.

(21) Appl. No.: 10/497,564

(22) PCT Filed: Dec. 3, 2002

(86) PCT No.: PCT/GB02/05440

§ 371 (c)(1),
(2), (4) Date: Dec. 14, 2004

(87) PCT Pub. No.: WO03/047613

PCT Pub. Date: Jun. 12, 2003

(65) Prior Publication Data

US 2006/0127895 A1 Jun. 15, 2006

(30) Foreign Application Priority Data

Dec. 3, 2001 (GB) .................................. 0128898.4

(51) Int. Cl.
*C12Q 1/66* (2006.01)
(52) U.S. Cl. .......................................... 435/8; 435/373
(58) Field of Classification Search ............... None
See application file for complete search history.

(56) References Cited

FOREIGN PATENT DOCUMENTS

| DE | 37 34 852 | 4/1989 |
|----|-----------|--------|
| EP | 0 599 077 | 6/1994 |
| JP | 09056836 | 4/1997 |
| WO | WO 94/09363 | 4/1994 |
| WO | WO 99/66946 | 12/1999 |

OTHER PUBLICATIONS

Rizzo et al. Postaglandins Leukotrienes and Essential Fatty Acids, vol. 60, No. 3, Mar. 1999, p. 187-198.*
Zaika et al. (The J. of Biological Chemistry, vol. 276, pp. 11310-11316, Apr. 2001).*
el-Deiry et al. (Curr. Opin. Oncol. vol. 9(1), pp. 79-87, 1997).*
Zaika, A., et al., "Oncogenes Induce and Activate Endogenous p73 Protein," The Journal of Biological Chemistry, 276:11310-11316 (2001).
Nabhan, J.F., et al., "A *Schistosoma mansoni* Pad1 homologue stabilizes c-Jun," Molecular & Biochemical Parasitology, 116:209-218, (2001).
Rizzo, M.T., et al., "Arachidonic acid induces mobilization of calcium stores and c-jun gene expression: evidence that intracellular calcium release is associated with c-jun activation," Prostaglandins, Leukotrienes and Essential Fatty Acids, 60:187-198, (1999).
Hilberg, F., et al., "Embryonic stem (ES) cells lacking functional c-jun: consequences for growth and differentiation, AP-1 activity and tumorigenicity," Oncogene, 7:2371-2380, (1992).

* cited by examiner

*Primary Examiner*—Larry R. Helms
*Assistant Examiner*—Meera Natarajan
(74) *Attorney, Agent, or Firm*—Dann, Dorfman, Herrell & Skillman; Kathleen D. Rigaut, J.D.

(57) ABSTRACT

The invention concerns the increased stabilization and activation of p73, a homologue of p53. Specifically, the inventors have determined that c-Jun, a component of the AP-1 family of transcription factors, is necessary for stabilization and activation of p73. Thus, there is provided a mechanism for initiating an apoptotic pathway involving c-June and p73 which can be exploited to combat cancers, particularly those lacking a functional p53.

11 Claims, 10 Drawing Sheets

Egfp reporter can be activated by transfection of p53 or p73 in p53-null H1299 lung carcinoma cells

Figure 9

Cisplatin induces p73 activity in p53-null H1299 lung carcinoma cells

USE OF C-JUN OR C-JUN ACTIVATING AGENTS SUCH AS UV OR C-JUN N-TERMINAL KINASES (JNKS) FOR TREATING CANCER

The present application is a §371 application of PCT/GB02/05440 filed Dec. 3, 2002 which in turn claims priority to GB Application 0128898.4 filed Dec. 3, 2001. The entire disclosure of each of the above identified applications is incorporated by reference herein.

The present invention provides materials and method for stabilizing and activating a tumour suppressor gene. Particularly, the invention concerns the increased stabilization and activation of p73, a homologue of p53 and methods of treating cancer using p73 modulators.

The tumour suppressor protein, p53 has been well characterised and much work has been carried out on determining agents that have the ability to activate this protein. The main role of p53 in the cellular response to DNA damage is the mediation of cell cycle arrest. This allows DNA repair to occur before the cell resumes replication. In some cell types, p53 activation leads to the elimination of irreparably damaged cells by apoptosis.

P73 is the structural and functional homologue of the tumour suppressor gene product p53. However, p73, unlike its homologue p53, is only selectively activated by a subset of agents that activate p53, such as cisplatin treatment and gamma irradiation. Although the non-receptor tyrosine kinase, c-Abl, has been demonstrated to be required for p73 activation by both these agents, cisplatin treatment results in stabilization of p73 whereas gamma-irradiation does not lead to p73 stability (Gong J G et al., The tyrosine kinase c-Abl regulates p73 in apoptotic response to cisplatin-induced DNA damage, Nature 1999, Jun. 24, 399 (6738): 806-9; Yuan Z M et al., p73 is regulated by tyrosine kinase c-Abl in the apoptotic response to DNA damage, Nature 1999, Jun. 24, 399 (6738):814-7; Agami et al., Interaction of c-Abl and p73 alpha and their collaboration to induce apoptosis, Nature 1999, Jun. 24, 399 (6738): 809-13; White E. et al., DNA damage enables p73, Nature 1999, Jun. 24, 399 (6738): 734-5, 737), suggesting the involvement of other molecular determinants in regulating p73 activity. When activated, p73 has been shown to induce cell-cycle arrest and cell death in a p53-independent manner. As p73 is generally not mutated in human cancers, unlike p53 that is mutated in more than 50% of all human malignancies, efficient activation of p73 in cancer cells would be a possible way to eradicate cancers. However, the mechanism(s) of p73 activation is not well understood. As mentioned above, only c-Abl tyrosine kinase has been shown to phosphorylate p73 and activate its function.

Surprisingly, the present inventors have determined that c-Jun, a component of the AP-1 family of transcription factors, is necessary for stabilization and activation of p73. The inventors have found that cisplatin treatment of fibroblasts results in c-Jun activation that correlates with p73 induction. Absence of c-Jun results in defective p73 activation and concomitant resistance to cisplatin-induced apoptosis. c-Jun stabilizes p73, and p73 was found to be less stable in c-Jun$^{-/-}$ cells compared to wild-type cells, demonstrating that c-Jun is required to stabilize p73. Moreover, UV-irradiation, which is a potent inducer of c-Jun, results in stabilization of p73 in a c-Jun dependent manner. In addition, the inventors have determined that c-Jun binds to p73 in vivo and expression of c-Jun results in increased p73 half-life, resulting in concomitant enhancement of p73 mediated-transactivation. The inventors further show that c-Jun is required for p73-mediated apoptosis that can occur in the absence of c-Abl, indicating that c-Jun mediated p73 regulation can occur in a c-Abl independent manner. These exciting findings provide an apoptotic pathway involving c-Jun and p73, which can be exploited to combat cancers, particularly those lacking a functional p53. It also provides the ability to screen for substances capable of modulating, e.g. stimulating the c-Jun mediated p73 pathway.

Thus, at its most general, the present invention provides materials and methods for treating cancers via a c-Jun mediated p73 pathway. The invention further provides methods for determining activating agents of a c-Jun mediated p73 pathway. The invention also provides methods for determining substances that are capable of mimicking the activity of c-Jun in a c-Jun mediated p73 pathway.

In addition, the invention provides research tools comprising modified cell lines which enable substances to be tested for their ability to modulate the activity of p73 of c-Jun.

In a first aspect, the present invention provides a method of treating a cancer in a patient, said method comprising the step of administering to said patient a therapeutically effective amount of an activating agent that is capable of activating a c-Jun mediated p73 pathway.

The activating agent may be c-Jun or an active portion (maintaining the ability to activate/stabilize p73) thereof, or it may be a c-Jun activating agent e.g. JNKs or UV irradiation. Said c-Jun activating agent may be used in association with c-Jun and/or a p73 activating agent, such as cisplatin, taxol, gamma radiation etc.

Discussed below are methods for screening test substances for those capable of activating c-Jun. These c-Jun activating substances may be used in the method above to activate a c-Jun mediated p73 pathway.

The inventors have determined for the first time that c-Jun is required for mediation of p73. They have found that c-Jun acts to stabilize and to activate p73.

For those cancer cells overexpressing p73, e.g. cells of an epithelial origin, c-Jun may itself be an activating agent of p73 in that it can bring about p73 mediated apoptosis. Thus, it is clear that the administration of c-Jun or active potion thereof would be beneficial to a cancer suffering patient so as to activate p73 apoptosis of the cancer cells. As will be discussed below, a mimetic of c-Jun may also serve the same useful purpose.

However, in addition to this, the inventors have found that c-Jun can act to stabilize p73 thereby increasing the half life of expressed p73. The action of c-Jun therefore allows the administration of other p73 activating agents e.g. cisplatin, gamma radiation, campodacin, taxol etc. which can themselves mediate the p73 apoptotic pathway.

Thus, the activating agent may be c-Jun (including active portion or mimetic thereof), an activating agent of c-Jun, or an activating agent of p73 which works in association with c-Jun.

Therefore, in a second aspect the present invention further provides a method of treating cancer in a patient, said method comprising the step of administering to said patient a therapeutically effective amount of a c-Jun activating agent.

Although UV irradiation is a known activator of c-Jun, a preferred c-Jun activating agent is a member of the c-Jun N-terminal kinases (JNKs), e.g. JNK1, JNK2 and JNK3. Preferably the activating agent is JNK1.

Extracellular signals are transduced to the nucleus by highly conserved mitogen activated protein kinase (MAPK) cascades, which result in a variety of physiological effects, depending on the type of cell and stimulus. The MAPKs include the ERKs, which primarily transduce mitogenic signals, and the c-Jun N-terminal kinases (JNKs) and p38s, together known as stress activated protein kinases (SAPKs), which signal stress responses (Cobb et al., 1995, J Biol Chem. 270: 14843-14846; Marshall et al. 1995, Cell. 80: 179-185; Minden et al., 1997, Biochem Biophys Acta. 1333: F85-F104). However, proinflammatory and some form of mitogenic signals can also activate the JNKs (Minden et al., 1997, Biochem Biophys Acta. 1333: F85-F104). The MAPKs are themselves activated by MAPK kinases (MAPKK) which are in turn activated by the MAPKK kinases (MAPKKKs), thus establishing a chain of signaling events which culminate in the phosphorylation and activation of transcription factors (Karin and Hunter 1995, Curr Biol, 5: 747-757).

Upon stimulation, the activated JNKs phosphorylate transcription factors like c-Jun and ATF-2, which participate in the activation and formation of the AP-1 complex (Karin 1996, J Biol Chem, 270: 16483-16486). The JNK subgroup consists of three members—JNK1, JNK2 and JNK3—each with multiple isoforms generated through alternate splicing (Derijard et al. 1994, Cell 76: 1025-1037; Kallunki et al. 1994, Genes Dev. 8: 2996-3007; Mohit et al. 1995, Neuron, 14: 67-78). Combinatorial use of the various JNKs and their upstream kinases lead to differential regulation of substrate proteins in response to multiple stimuli. Among the three members of the JNK family, JNK3 is expressed predominantly in the brain whereas both JNK1 and JNK2 are expressed ubiquitously (Mohit et al. 1995, Neuron, 14: 67-78). The JNKs have been shown to bind to the delta domain of c-Jun and phosphorylate it on serines 63 and 73, leading to its activation (Kallunki et al. 1994, Genes Dev, 8: 2996-3007). Of the two, JNK2 has been shown to have a twenty-five fold higher binding affinity for c-Jun than JNK1 (Kallunki et al. 1994, Genes Dev, 8: 2996-3007). Moreover, although the various isoforms of both JNK1 and JNK2 were shown to bind and phosphorylate the substrates to various extents in in vitro experiments, the JNK1 isoforms appear to be slightly more efficient in phosphorylating c-Jun (Gupta et al. 1996, EMBO J. 15:2760-2770). It thus seems that the different JNK isozymes may have evolved for specific biological functions, probably depending on the activating stimuli and responding cell type.

Of the three members of the Jun family of transcription factors, JNKs phosphorylate c-Jun very efficiently, JunD less efficiently, but they do not phosphorylate JunB (Kallunki et al. 1996, Cell. 87: 929-939). Effective JNK substrates require a separate docking site (the delta domain) and specificity-conferring residues flanking the phosphoacceptor site. The docking site increases the efficiency and specificity of the phosphorylation reaction. JunB has a functional JNK docking site but lacks specificity-conferring residues (Kallunki et al. 1996, Cell. 87: 929-939). JunD, by contrast, lacks a JNK docking site, but its phosphoacceptor peptide is identical to that of c-Jun (Kallunki et al. 1996, Cell. 87: 929-939). Substrates such as JunD can be phosphorylated by JNK through heterodimerization with docking competent partners. Therefore, heterodimerization can affect the recognition of transcription factors by signal-regulated protein kinases. Hitherto, most in vitro studies have used c-Jun as the model substrate to investigate the nature of JNK-substrate binding activity and specificity.

The activating agent, e.g. c-Jun, may be administered in the form of an active polypeptide, active in that it is capable of mediating p73 activity. Alternatively, a nucleic acid molecule may be administered that is capable of expressing an active c-Jun polypeptide. The nucleic acid may be wholly or partially synthetic and may include genomic DNA, cDNA or RNA. The nucleic acid may form part of a nucleic acid expression vector which may in turn comprise control sequences operably linked to the c-Jun nucleic acid to control its expression. The vectors may include other sequences such as promoters or enhancers to drive the expression of the inserted nucleic acid.

The administration of the p73 activating agent, the c-Jun, c-Jun mimetic the c-Jun activating agent, or combination thereof may conveniently be administered in the form of a gene therapy vector.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively, the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovavirus, such as SV40, vaccinia virus, herpes virus, including HSV and EBV, and retrovirus.

As an alternative to the use of viral vectors other known methods of introducing nucleic acid into cells includes electroparation, calcium phosphate co-precipitation, mechanical techniques such as microinjection, transfer mediated by liposomes and direct DNA uptake and receptor mediated DNA transfer.

As mentioned above, the aim of gene therapy using nucleic acid encoding c-Jun, p73 and/or an activating agent of c-Jun (e.g. JNKs) and an activating agent of p73, is to increase the amount of expressed product of the nucleic acid in cells where they will be biologically active, i.e. mediate a p73 apoptotic pathway in cancer cells. Such treatment maybe therapeutic in the treatment of cells which are already cancerous or prophylactic in the treatment of individuals known through screening to have a cancer susceptibility.

A vector may comprise nucleic acid encoding c-Jun, an active portion or mimetic thereof, a p73 activating agent, a c-Jun activating agent or a combination thereof.

In a preferred embodiment, the vector comprises nucleic acid encoding at least the active portion (p73 mediating) of c-Jun and optionally a p73 activating agent. The nucleic acid may encode the two components as a fusion protein.

In a preferred embodiment, the method according to the first or second aspect of the invention may also comprise the step of administering c-Jun or active portion or mimetic thereof in association with p73 or functional fragment thereof. A functional fragment of p73 is one that is capable of bringing about cell cycle arrest and/or bringing about apoptosis of a cell, preferably a cancer cell. An active portion of c-Jun is that portion that is capable of stabilizing and/or activating p73.

The present invention further provides the use of c-Jun, c-Jun activating agent, p73 activating agent, combination thereof or functional equivalent thereof, and optionally p73, in the preparation of medicament for treating cancers.

Given the importance of c-Jun in the stabilization and activation of p73, it may be preferably to use a substance whose biological activity is functionally equivalent to c-Jun, e.g. a mimetic as mentioned above.

A functional equivalent of c-Jun may be a peptidyl molecule, e.g. a polypeptide or peptide derived from c-Jun, or non-peptidyl molecule, e.g. mimetic, that is capable of carrying out the equivalent biological function as c-Jun in relation to p73.

In a third aspect of the present invention, there is provide a method of screening for such functionally equivalent substances.

Thus, the invention provides a method for screening for substances that have the ability to affect or modulate the activity of c-Jun, p73 or c-Jun's mediation of p73. Such substances may be useful in a therapeutic context.

For example, it may be desirable to screen for substances that are capable of mimicking the activity of c-Jun in relation to the stabilisation and activation of p73. Alternatively, it may be desirable to screen for substances that are capable of modulating e.g. increasing/improving the c-Jun mediation of p73.

It is well known that pharmaceutical research leading to the identification of a new drug may involve the screening of very large numbers of candidate substances, both before and even after a lead compound has been found. This is one factor that makes pharmaceutical research very expensive and time-consuming. Means for assisting in the screening process can have considerable commercial importance and utility. Such means for screening for substances potentially useful in treating or preventing cancer is provided by c-Jun and p73 association determined by the present inventors. Substances identified as modulators of the c-Jun/p73 interaction represent an advance in the fight against cancer since they provide basis for design and investigation of therapeutics for in vivo use.

A method of screening for a substance which modulates activity of p73 polypeptide or a c-Jun polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances. The activity is preferably the ability of c-Jun to mediate p73 stabilisation and activity.

Combinatorial library technology provides an efficient way of testing a potentially vast number of different substances for ability to modulate activity of a polypeptide. Such libraries and their use are known in the art. The use of peptide libraries is preferred.

Following identification of a substance which has the ability of c-Jun to modulate or affect p73 activity and/or stabilization, the substance may be investigated further. Furthermore, it may be manufactured and/or used in preparation, i.e. manufacture or formulation, of a composition such as a medicament, pharmaceutical composition or drug. These may be administered to individuals.

A test substance that is found to mimic the activity of c-Jun in its ability to stabilise and activate p73 may be used as a mimetic. The inventor's determination that c-Jun has the ability to activate p73 opens up the possibility of directly producing mimetics of c-Jun.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound.

Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

In order to identify c-Jun mimetics in activating p73, the inventors have generated cells stably-expressing p73. Upon UV irradiation, a potent inducer of c-Jun but not p73 (other inducers or activators of c-Jun could be used), there was an increase in the levels of p73 in these cells. This occurs in a c-Jun dependent manner, as the increase in p73 after UV irradiation is not observed in c-Jun−/− cells. Thus, both the wild-type and c-Jun−/− cells stably-expressing p73 and carrying a p53/p73 binding-site driving the luciferase gene can be used to identify c-Jun mimetics or compounds that activate p73 in a c-Jun dependent manner. The inventors used luciferase as a reporter here so that they could quantify the effect of the c-Jun mimetics on the already expressed basal p73 activity. However, it will be apparent to the skilled person that other known means of detecting expression may be used, e.g. green fluorescent protein gene (Egfp).

In addition, other screens can be established to identify factors that can activate c-Jun, thus leading to p73 activation. The inventors have found that c-Jun can be activated to low levels in cells lacking both JNK1 and JNK2 (common activators of c-Jun), indicating that there are other activators of c-Jun besides JNKs. Thus, as an example of such screening methods, Jnk1−/−Jnk2−/− cells may be used to identify activators of c-Jun either mimetics of JNKs or others. In these cells, the reporter used is the Ap-1 binding-site driving the luciferase gene but others may equally be used. C-Jun binds to the Ap-1 site and drives transcription of the luciferase gene. Thus, the Jnk1−/−Jnk2−/− cells can be treated with various compound libraries to identify activators of c-Jun in the absence of the JNKs.

In addition, the c-Jun−/− cells expressing the Ap-1 binding-site driving the luciferase gene can be used to screen for activators of c-Jun mimetics or compounds that can substitute for the absence of c-Jun.

Besides these, the inventors have also devised screening methods using the principle of JNK binding to c-Jun to identify peptides and compounds that can interfere with this binding. Normal (wild-type) cells expressing the Ap-1 binding-site driving the luciferase gene would have a certain amount of Ap-1 activity due to the endogenous levels of c-Jun present. Addition of peptides or compounds that interfere with c-Jun/Jnk binding would thus result in the loss or decrease of the Ap-1 activity. Such compounds could then be used as mimetics of JNKs to activate c-Jun, and its efficacy can be tested in cells lacking JNK1 and JNK2 and expressing the Ap-1 binding-site driving the luciferase gene.

Thus in summary, the invention provides screens for substances that activate c-Jun, i.e. increase its ability to mediate p73 stabilization and activation. Further, the invention provides screens for substances that mimic the activity of c-Jun in relation to its ability to mediate p73 function.

Accordingly, the invention provides a method of screening for substances which mimic the activity of a c-Jun polypeptide, the method comprising contacting the test substances with p73 in a suitable environment and determining whether the test substances have the ability to stabilize/activate p73 as compared to the ability of c-Jun to stabilize/activate p73.

The ability to stabilize/activate p73 may conveniently be determined by using a p73 binding site in association with a reporter gene, e.g. luciferase or Egfp.

Suitable environments for such screening methods may be cells that are render deficient in a factor under test. In other words, if one wanted to screening for mimetics of c-Jun, use of c-Jun$^{-/-}$ cells would provide an appropriate environment. The results could be compared with those following identical testing but using a wild type cell possessing endogenous c-Jun.

Further, there is provided a method of screening for substances which affect or modulate the ability of c-Jun to mediate the stabilization and/or activation of p73, the method comprising the steps of contacting one or more substances with c-Jun and p73 in a reaction medium; testing the stabilization and/or activation of the treated p73 and comparing that stabilization and/or activity with the stabilization and/or activity of the p73 polypeptide in comparable reaction medium untreated with the test substances or substance.

Again, the ability to stabilize/activate p73 may conveniently be determined by using a p73 binding site in association with a reporter gene, e.g. luciferase or Egfp.

In order to carry out the screening methods described above, the inventors have engineered several cell lines which may be used as research tools.

Thus, as a further aspect of the present invention, there is provided a stable cell line (prokaryotic, eukaryotic, mammalian or bacterial cell line) which produces c-Jun$^{-/-}$ cells comprising a nucleic acid construct having a p73 binding domain or an Ap-1 binding domain, each capable of driving the expression of a reporter gene such as luciferase or EgFp.

Alternatively, the cell line may produce Jnk1$^{-/-}$ Jnk2$^{-/-}$ cells comprising a nucleic acid construct having a p73 binding domain or an Ap-1 binding domain, each capable of driving the expression of a reporter gene such as luciferase or EgFp.

Aspects and embodiments of the present invention will now be illustrated, by way of example, with reference to the accompanying figures. Further aspects and embodiments will be apparent to those skilled in the art. All documents mentioned in this text are incorporated herein by reference.

In the figures:

FIG. 3. c-Jun stabilizes p73. (a) Effect of c-Jun on p73-beta levels in COS7 cells. COS7 (lanes 1-4) were transfected transiently with the plasmids encoding c-Jun, p73-beta or in combination, or vector (PCDNA) as indicated. 48 hours later, cell extracts were prepared and Western-blotted, and proteins were detected with anti-p73 (GCI5), anti-c-Jun (H79) and anti-actin antibodies. (b) Wild-type, c-Jun$^{-/-}$ and c-Jun$^{-/-}$+c-Jun mouse embryonic fibroblasts were transiently transfected with plasmids encoding p73-beta alone or in combination with c-Jun and cell extracts were analyzed by Western blotting as described in FIG. 1. (c) Half-life determination. COS7 cells were transfected with p73-beta and c-Jun plasmids or p73-beta alone and pulse labeled with $^{35}$S-Met/Cys followed by a six-hour chase. P73 expression was detected by autoradiography.

Figure 1:
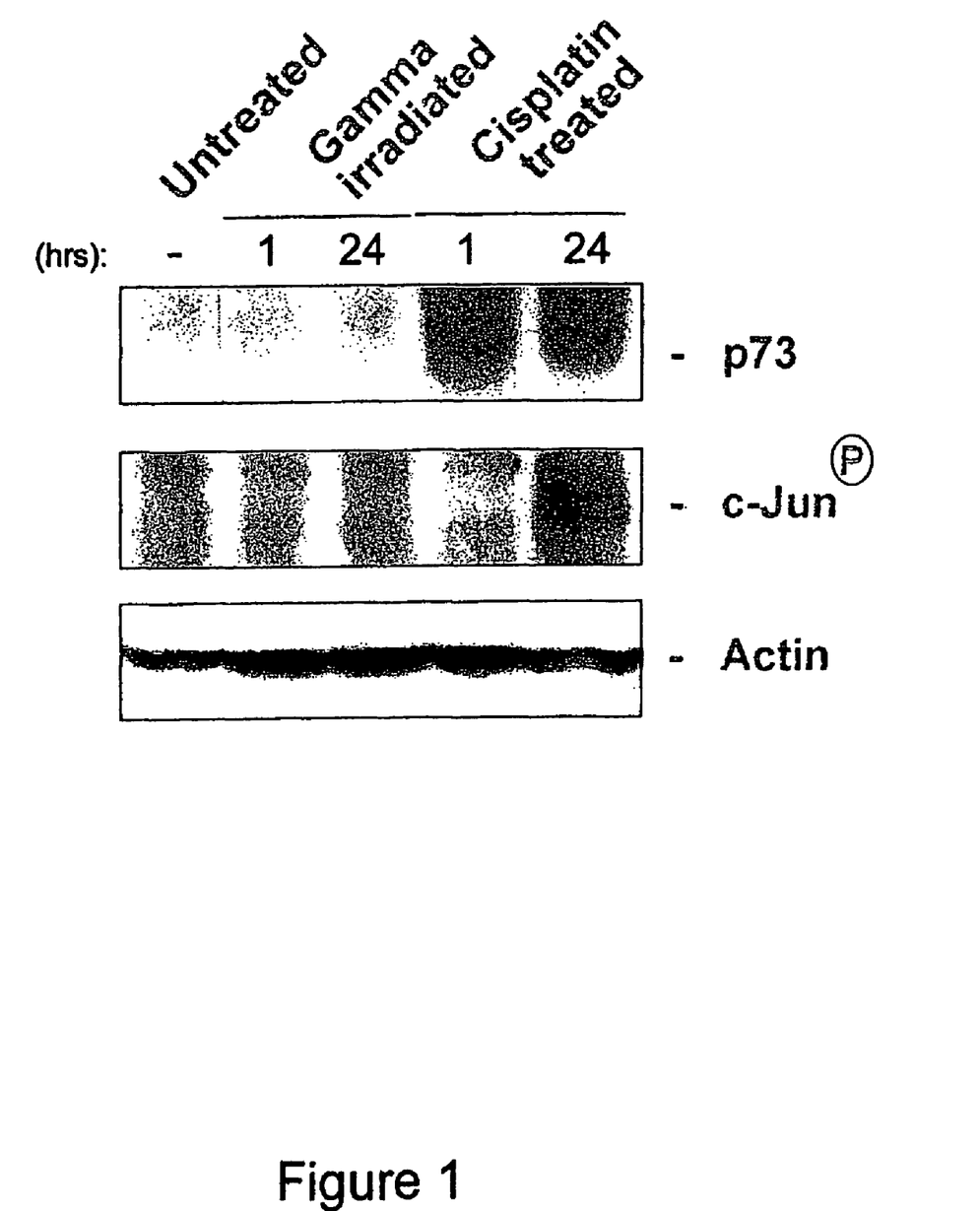
FIG. 1. Cisplatin but not gamma-irradiation results in detectable expression of p73. Wild-type mouse embryonic fibroblasts were treated with either cisplatin (25 mM) or gamma-irradiated (20Gy) and cells extracts were prepared 1 or 24 hours post treatment. These extracts were analysed by Western blotting for the expression of p73 and phosphorylated c-Jun using specific antibodies.
Figure 2:
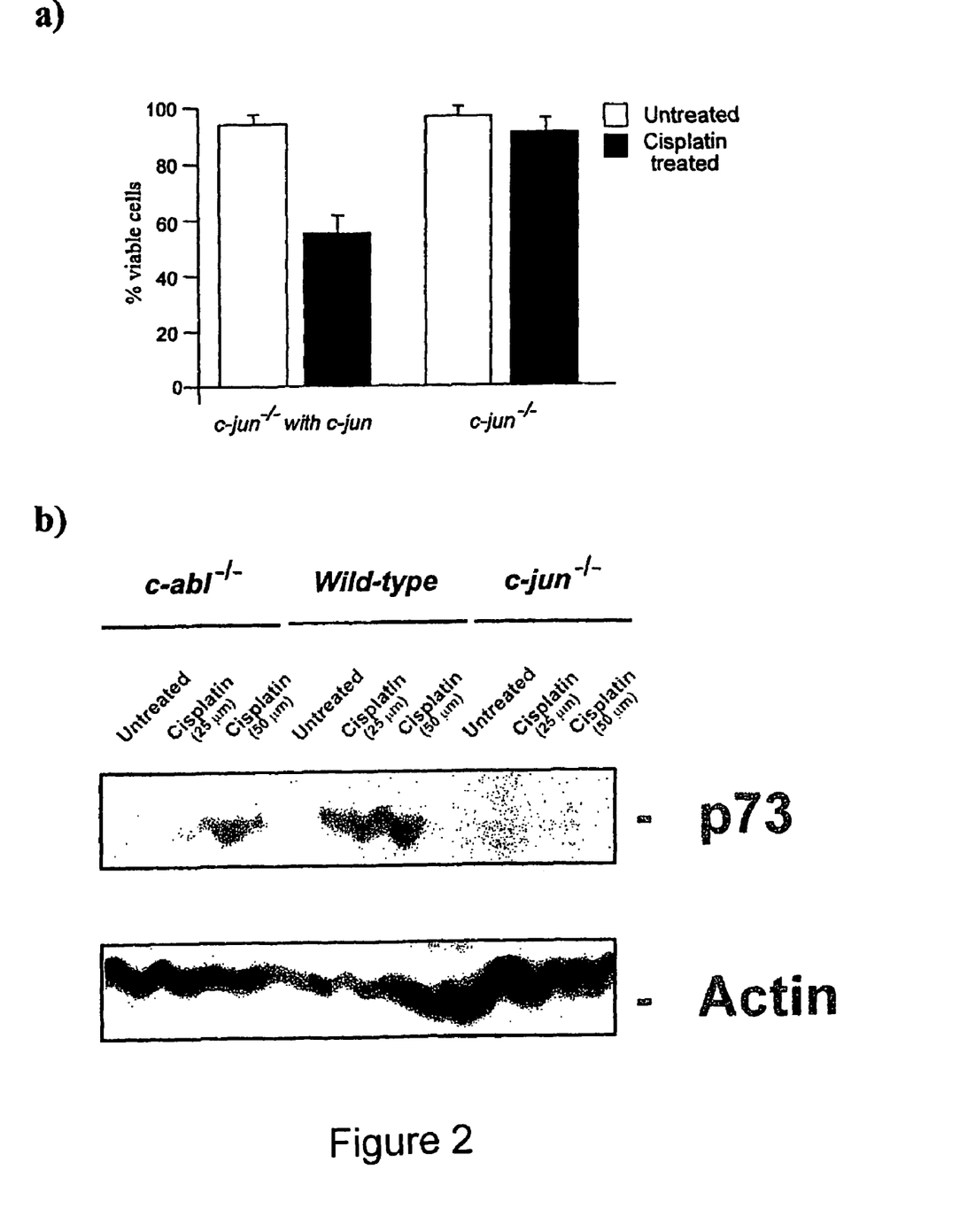
FIG. 2. c-Jun is necessary for cisplatin-induced p73 expression and apoptosis. (a) Wild-type, c-Jun$^{-/-}$ and c-Jun$^{-/-}$ mouse embryonic fibroblasts stably transfected with c-Jun were treated with cisplatin (25 μM) for 24 hours and the extent of cell death was determined by staining cells with annexin-VFitC and subsequent flow cytometric analysis. (b) Extracts from cells described in (a) were analyzed for endogenous p73 levels by Western blotting.

Although p73 is a structural and functional homologue of the p53 tumour suppressor protein, p73 is only activated by a subset of agents that activate p53. Unlike p53 that is stabilized by most signals, p73 protein levels do not increase upon exposure of cells to gamma irradiation, a potent p73 inducer. However, p73 is stabilized in cells treated with the apoptosis inducing agent, cisplatin (1). The inventors have thus investigated the molecular mechanism(s) by which p73 activity is regulated. As previously suggested, treatment of fibroblasts with gamma-irradiation does not result in an increase in the levels of p73 over time (FIG. 1). In contrast, cisplatin treatment of these cells resulted in an increase in the levels of p73 protein, which was observed at 24 hours post-treatment (FIG. 1). The increase in p73 levels in cisplatin-treated cells correlates with the phosphorylation of the proto-oncogene product, c-Jun (FIG. 1). Phosphorylated c-Jun was not detected upon gamma-irradiation of cells (FIG. 1). To examine if c-Jun has any role in regulating p73 activity, the inventors investigated the response of c-Jun deficient cells to cisplatin. Treatment of fibroblasts with 25 μm of cisplatin resulted in a significantly reduced amount of cell death in c-Jun$^{-/-}$ fibroblasts compared to both c-Jun$^{-/-}$ cells reconstituted with c-Jun (jun$^{-/-}$+c-Jun) and wild-type cells, 24 hours post-treatment (viable c-jun$^{-/-}$ cells: 93%; viable jun$^{-/-}$+c-Jun cells: 52%) (FIG. 2a). Western blot analysis of p73 expression revealed that p73 protein was induced significantly in jun$^{-/-}$+ c-Jun cells (FIG. 2b). In contrast, absence of c-Jun abrogated the induction of p73 (FIG. 2b). p73 induction was also severely compromised in the absence of c-Abl, consistent with previously published data (2) (FIG. 2b). Together, these results demonstrate that c-Jun is required for efficient p73 expression upon cisplatin treatment.

Figure 3:
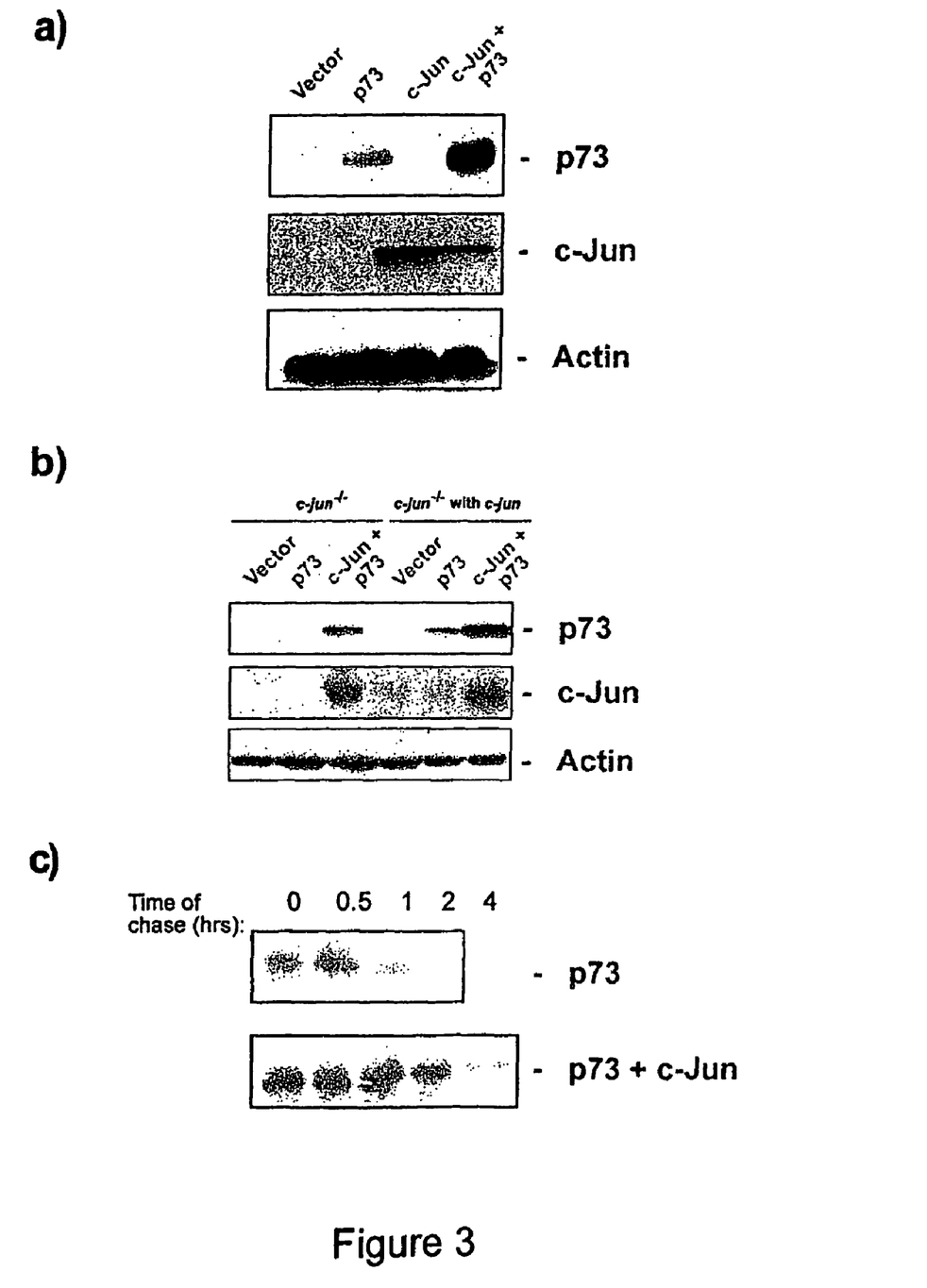

In an attempt to understand the role of c-Jun in regulating p73 expression and activity, transient transfection experiments were carried out in COS7 and H1299 cells. Co-expression of c-Jun with p73 resulted in a dramatic increase in the levels of p73 compared to expression of p73 alone (FIG. 3a, compare lanes 2 to 4). In contrast, expression of c-Jun did not affect the levels of the green fluorescent protein (Egfp), which was used to normalize the transfection efficiency (FIG. 3a, lanes 1-4). The increased levels of p73 in the presence of c-Jun was not due to increased p73 transcription, as the levels of p73 mRNA remained constant in the presence of c-Jun (data not shown). To confirm that c-Jun was indeed required for efficient stabilization of p73, the inventors expressed p73 in mouse fibroblasts lacking c-Jun and in jun$^{-/-}$+c-Jun cells. Levels of p73 expression was much reduced in c-Jun$^{-/-}$ fibroblasts as compared to the jun$^{-/-}$+c-Jun cells (FIG. 3b, lanes 2 to 5). Transient expression of c-Jun together with p73 in c-Jun$^{-/-}$ fibroblasts resulted in higher levels of p73 expression (FIG. 3b, lanes 2 to 3). In addition, expression of c-Jun with p73 in jun$^{-/-}$+c-Jun cells led to the highest levels of p73 expression (FIG. 3b, lane 6). Thus, to investigate if c-Jun regulates p73 at the post-transcriptional level, the stability of p73 protein was determined. Transfected COS7 cells were pulse labeled with $^{35}$S-Met/Cys followed by a six-hour chase (FIG. 3c). Transiently expressed p73 had a half-life of about 45 minutes (FIG. 3c: p73 alone). When p73 was co-expressed with c-Jun, its half-life increased to 3 hours (FIG. 3c: p73+c-Jun). This stabilization was seen in several other human cell lines including H1299, MCF-7 and 293 cells (data not shown). The results demonstrate that c-Jun contributes to accumulation of p73 in both human and mouse cells.

Figure 4:
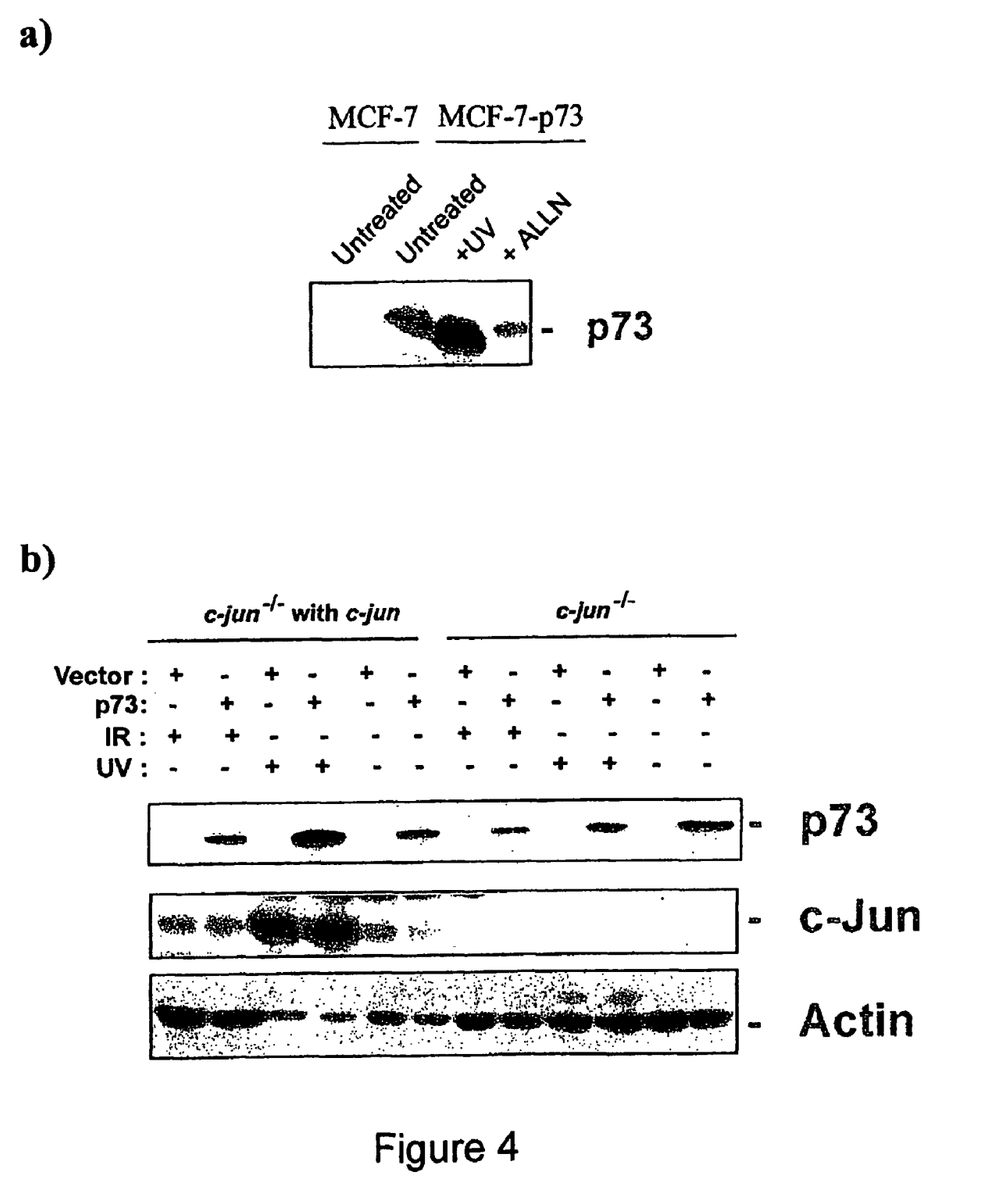
FIG. 4. c-Jun is required for UV-mediated p73 stabilization. (a) MCF-7 cells stably transfected with p73 and parental MCF-7 cells were treated with the proteosome inhibitor for 3 hours or UV irradiated (50 J/m$^2$) and cell extracts were analyzed 2 hours post-irradiation by Western blotting as described in FIG. 1. (b) c-Jun$^{-/-}$ and c-Jun$^{-/-}$+c-Jun mouse embryonic fibroblasts were transfected with the indicated plasmids and were untreated or UVC irradiated (40 J/m$^2$) or gamma-irradiation (10Gy) 24 hours post-transfection. 24 hours after irradiation, cell extracts were prepared and analyzed for p73 protein levels by Western blotting.

Many growth and stress signals result in c-Jun phosphorylation and hence activation, but do not result in p73 expression (Shaulian E. et al., The mammalian UV response: c-Jun induction is required for exit from p53-imposed growth arrest, Cell, 2000, Dec. 8, 103(6):897-907), probably because the inductive signal for p73 is absent. To analyze if c-Jun provides the stabilization signal, the inventors generated MCF-7 breast carcinoma cells stably expressing p73 (MCF-7-p73 cells), which would thus provide a detectable level of basal p73 expression. The overexpressed p73 was expressed in these cells (FIG. 4a). The inventors also investigated if the overexpressed p73 is actively degraded by the proteosome-mediated degradation machinery in the cell. Treatment of MCF-7-p73 cells with the proteosome inhibitor ALLN did not result in the increased expression of p73 protein, indicating that p73 is not degraded by the proteosome pathway (FIG. 4a). However, when these cells were treated with UV irradiation, which is a potent inducer of c-Jun but not p73 (Jost C A. et al, p73 is a simian [correction of human] p53-related protein that can induce apoptosis, Nature, 1997, Sep. 11; 389 (6647):191-4.), p73 expression was detected as early as 2 hours post-irradiation, in contrast to the parental MCF-7 cells (FIG. 4a). The UV-induced expression of p73 in MCF-7-p73 cells correlated with the appearance of phosphorylated c-Jun protein (data not shown), indicating that the expression of c-Jun leads to p73 stabilization.

In order to further confirm the role of c-Jun in p73 stability, wild-type and c-Jun$^{-/-}$ fibroblasts were transfected with p73 plasmids and treated with UV irradiation. As shown in FIG. 4b, UV irradiation resulted in increased levels of p73 in wild-type fibroblasts, in contrast to those lacking c-Jun, providing genetic evidence that c-Jun is essential for providing the signal necessary for the stabilization of p73. In contrast, gamma irradiation which does not induce c-Jun did not result in the stabilisation of p73 (FIG. 4b). Moreover, the transfected p73 protein was stabilized by UV irradiation in c-Abl$^{-/-}$ cells, indicating that c-Jun mediated p73 stabilization occurs either independent or downstream of c-Abl induced p73 phosphorylation/induction (data not shown).

Figure 5:
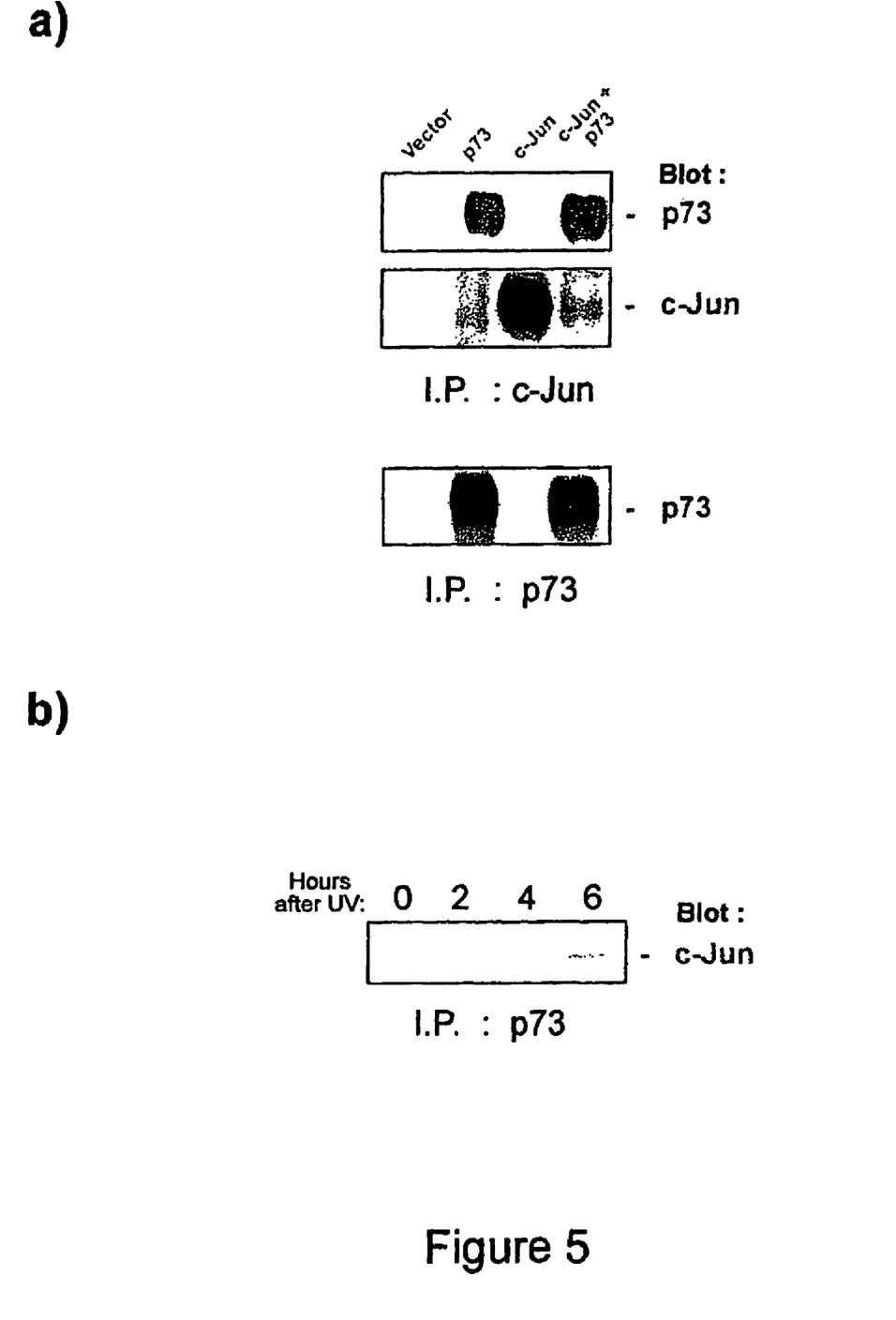
FIG. 5. c-Jun interacts with p73. (a) COS7 cells were transfected transiently with p73-beta, c-Jun or in combination and cell extracts were immunoprecipitated with anti-c-Jun or anti-p73 antibodies and immunoblotted with the indicated antibodies. (b) MCF-7-p73 cells were UV irradiated (50 J/m$^2$) and cell extracts prepared 2 hours post-irradiation were used for immunoprecipitation experiments as described above.

The inventors next examined if there was molecular interaction between c-Jun and p73. To this end, COS7 cells were transfected with either p73 alone or with c-Jun and the cell extracts were immunoprecipitated with antibodies against either p73 or c-Jun and analyzed by Western blotting. Immunoprecipitates of p73 was found to contain c-Jun in the complex and vice versa (FIG. 5a). To confirm if the interaction occurred at the physiological levels, MCF-p73 cells were UV irradiated and immunoprecipitations were carried out. In these cell extracts, c-Jun was also found in a complex with p73 (FIG. 5b), indicating that c-Jun directly binds to p73 which probably leads to p73 stability.

Figure 6:
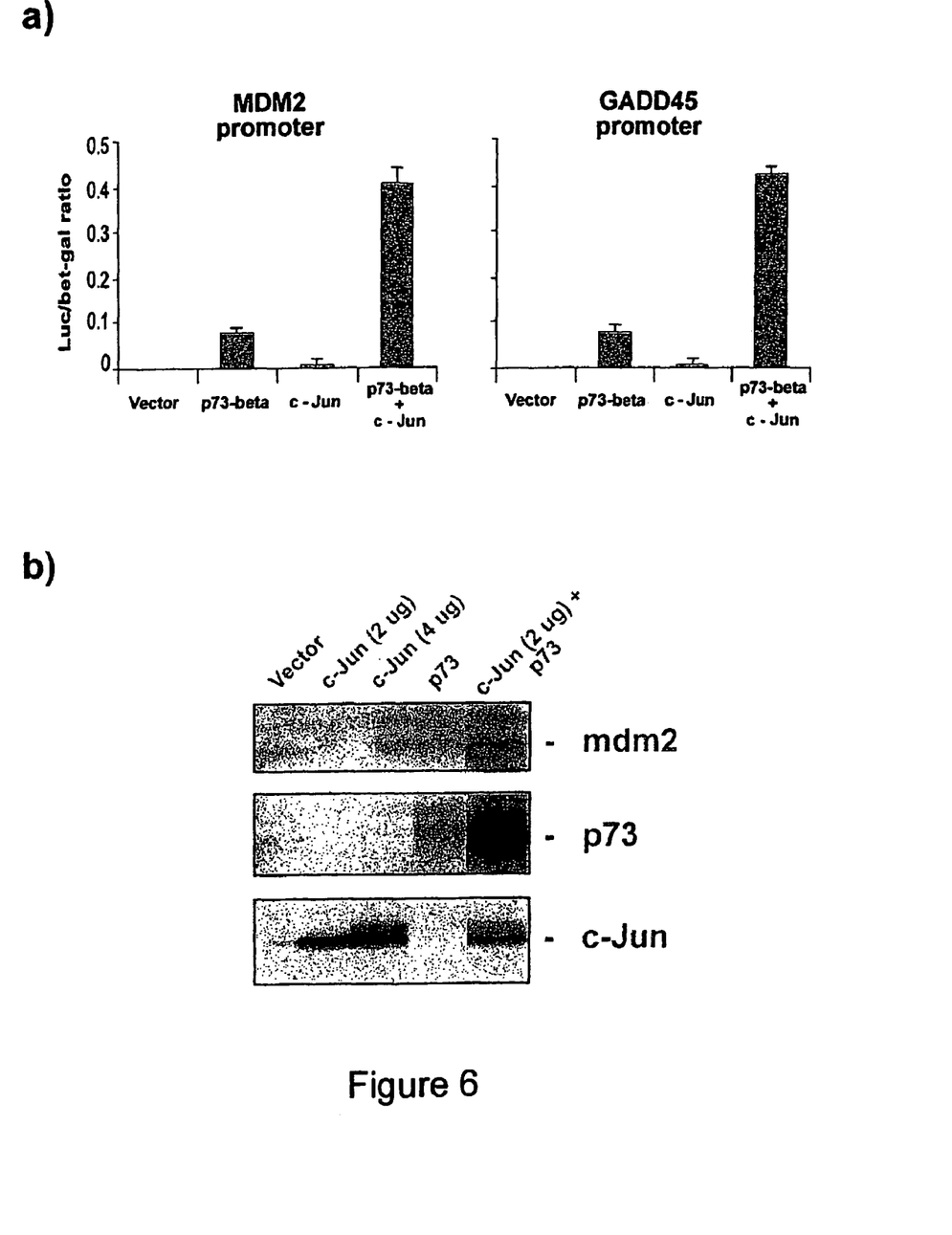
FIG. 6. p73 transactivation is induced by c-Jun. (a) The indicated plasmids were transfected into H1299 cells with a reporter plasmid containing the mdm2 promoter driving the luciferase gene or the gadd45 promoter driving the luciferase gene, together with a plasmid encoding the beta-galactosidase gene for evaluating the transfection efficiency. Cell extracts were analyzed 48 hours post transfection for beta-galactosidase and luciferase activity. (b) Extracts from COS7 cells transfected with the indicated plasmids were prepared 48 hours post transfection and the levels of the endogenous hdm2 protein was determined by Western blotting.

The inventors next determined if the stabilised p73 is transcriptionally more active. Reporter assays were performed in H1299 cells which were transfected with various combinations of c-Jun, p73 and various p53/p73 responsive promoter constructs driving the luciferase gene. As expected, expression of p73 resulted in an induction of the targets leading to expression of luciferase activity (FIG. 6a). Co-transfection of c-Jun with p73 resulted in a marked increase in the transcriptional activity, indicating that the activity of p73 is potentiated in the presence of c-Jun, thus correlating activity to the expression levels. The inventors further examined if the co-expression of c-Jun and p73 would lead to upregulation of p73 target gene products in vivo. Both c-Jun and p73 were transfected in COS7 cells as indicated and the levels of mdm2 was analyzed. The levels of mdm2 was upregulated in cell extracts of c-Jun/p73 transfectants compared to p73 transfectants alone (FIG. 6b), indicating that c-Jun mediated p73 stability results in potentiation of p73 transcriptional activity.

Figure 7:
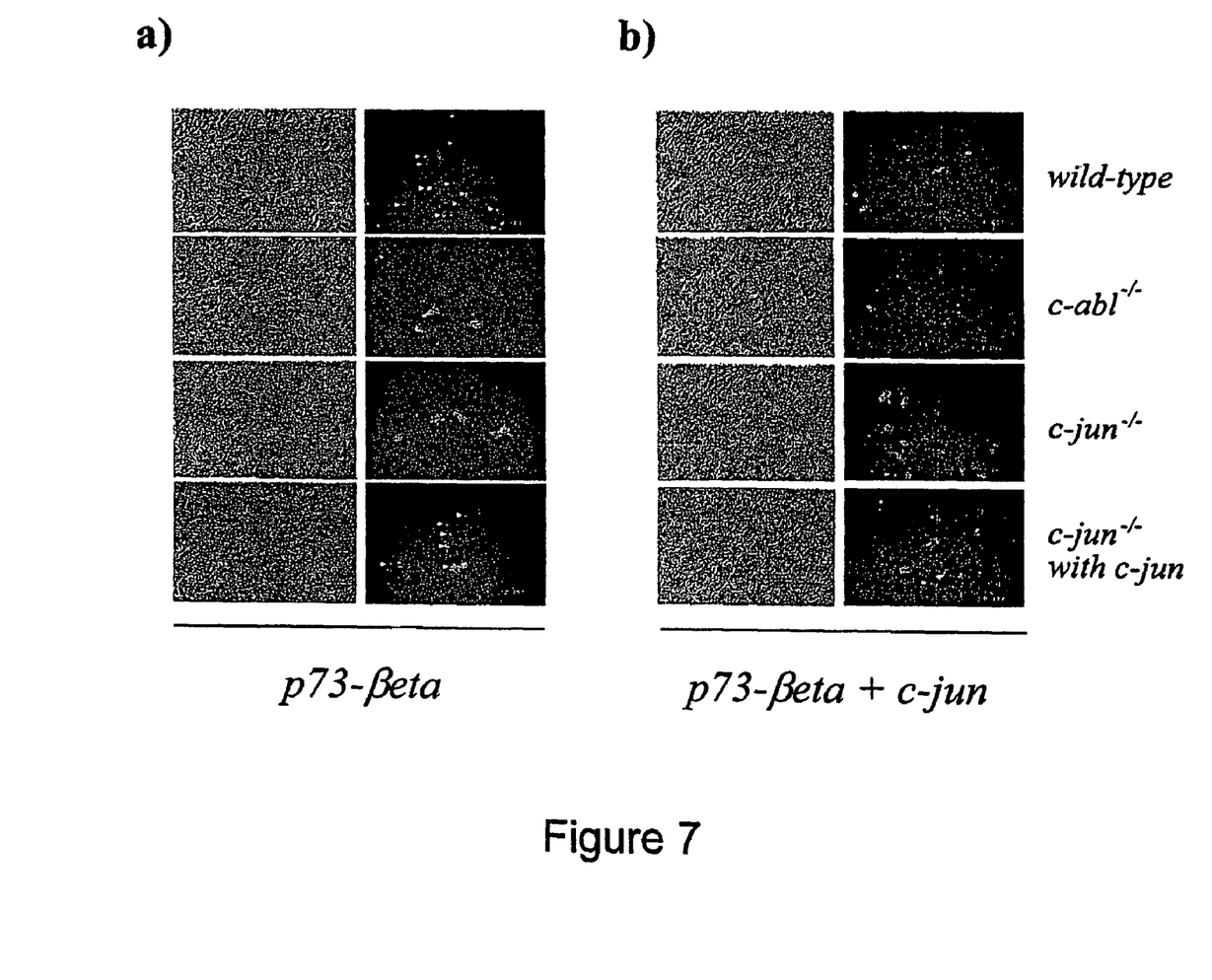
FIG. 7. C-Jun is required for p73 mediated cell-death. Wild-type, c-Jun$^{-/-}$ and c-Jun$^{-/-}$+c-Jun and c-abl$^{-/-}$ mouse embryonic fibroblasts were transfected with plasmids encoding p73-beta and egfp (a) or in combination with c-Jun (b) and were visualized for cell-death based on morphological changes. Egfp expression indicates transfected cells. The arrow heads indicate cells which are undergoing cell-death.

The inventors finally investigated the physiological significance of c-Jun mediate p73 stabilization by evaluating if p73-mediated cell death requires the co-operation with c-Jun. Wild-type mouse fibroblasts, c-Jun$^{-/-}$, c-abl$^{-/-}$ and jun$^{-/-}$+c-Jun cells were transiently transfected with the p73 expression plasmid together with the Egfp plasmid to identify successfully transfected cells. Analysis of cells under fluorescence microscopy indicated that many of the p73 transfected wild-type cells were undergoing cell death as ascertained by their morphology (FIG. 7a). In contrast, p73 transfected c-Jun$^{-/-}$ cells were viable and healthy, similar to the p73-transfected c-abl$^{-/-}$ cells (FIG. 7a). In addition, p73-mediated cell death was restored in jun$^{-/-}$+c-Jun cells, indicating that c-Jun is required for efficient p73-mediated cell death (FIG. 7a). Moreover, co-transfection of p73 and c-Jun plasmids resulted in cell death of c-Jun$^{-/-}$ cells, further confirming that c-Jun is required for p73-mediated apoptosis. Furthermore, c-Jun and p73 collaborated to induce cell death in the absence of c-Abl, suggesting that c-Jun regulates p73 in a manner independent or downstream of c-Abl (FIG. 7b).

The data demonstrates that c-Jun is a critical component in the regulation of p73 protein function. p73, although being similar in many aspects to its counterpart p53, is not mutated in human cancers (Levrero M, et al, The p53/p63/p73 family of transcription factors: overlapping and distinct functions, J Cell Sci. 2000 May; 113 (Pt 10):1661-70. Review), in contrast to p53. Moreover, genetic data from p73 knockout mice has indicated that the primary function of p73 might be in regulating development processes rather than serving in the first line of defence against cancer. Thus, identification of efficient methods or molecular pathways for the activation of the latent p73 in tumour cells can be exploited to enhance its tumour-suppressor function, leading to eradication of cancer. The inventor's data shows that c-Jun is a molecular component required for p73 activation which can thus be exploited for the clinical activation of p73 using c-Jun gene itself in gene-therapeutic programs or using c-Jun mimetics.

With regard to the second aspect of the present invention, the inventors have devised a cell-based screening method for activators of p73.

Figure 8:
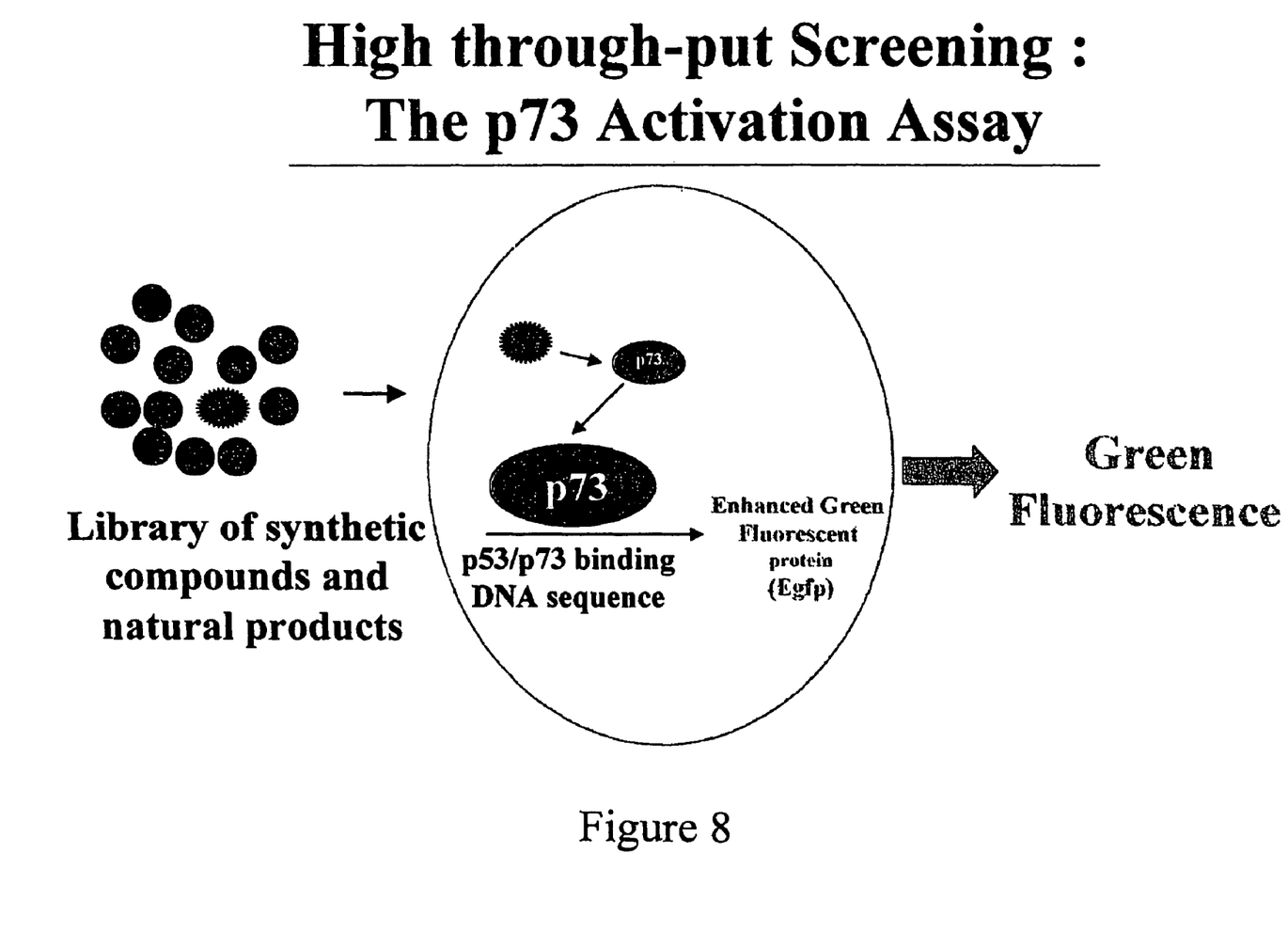
FIG. 8 illustrates high through-put screening assay for p73 activation.

The screen utilises a p53 null cell line, H1299, which is a human lung cancer cell line. In these cells, p53 is not active as the gene is deleted. The inventors have transfected a plasmid containing the p53/p73 binding DNA sequences (or responsive element) driving the enhanced green fluorescent protein gene (Egfp) as a reporter (FIG. 8). Generally, the reporter would be turned "on" when p53 or its homologues bind to the responsive element. In our HI299-p53RE cells, agents that activate p53 would not turn "on" the Egfp and hence, the cells would be colourless. However, when the cells are exposed to compounds that activate p73, which is normally present in a dormant state in these cells, then these cells would fluoresce and would be visible as green cells under the fluorescence microscope.

Figure 9:
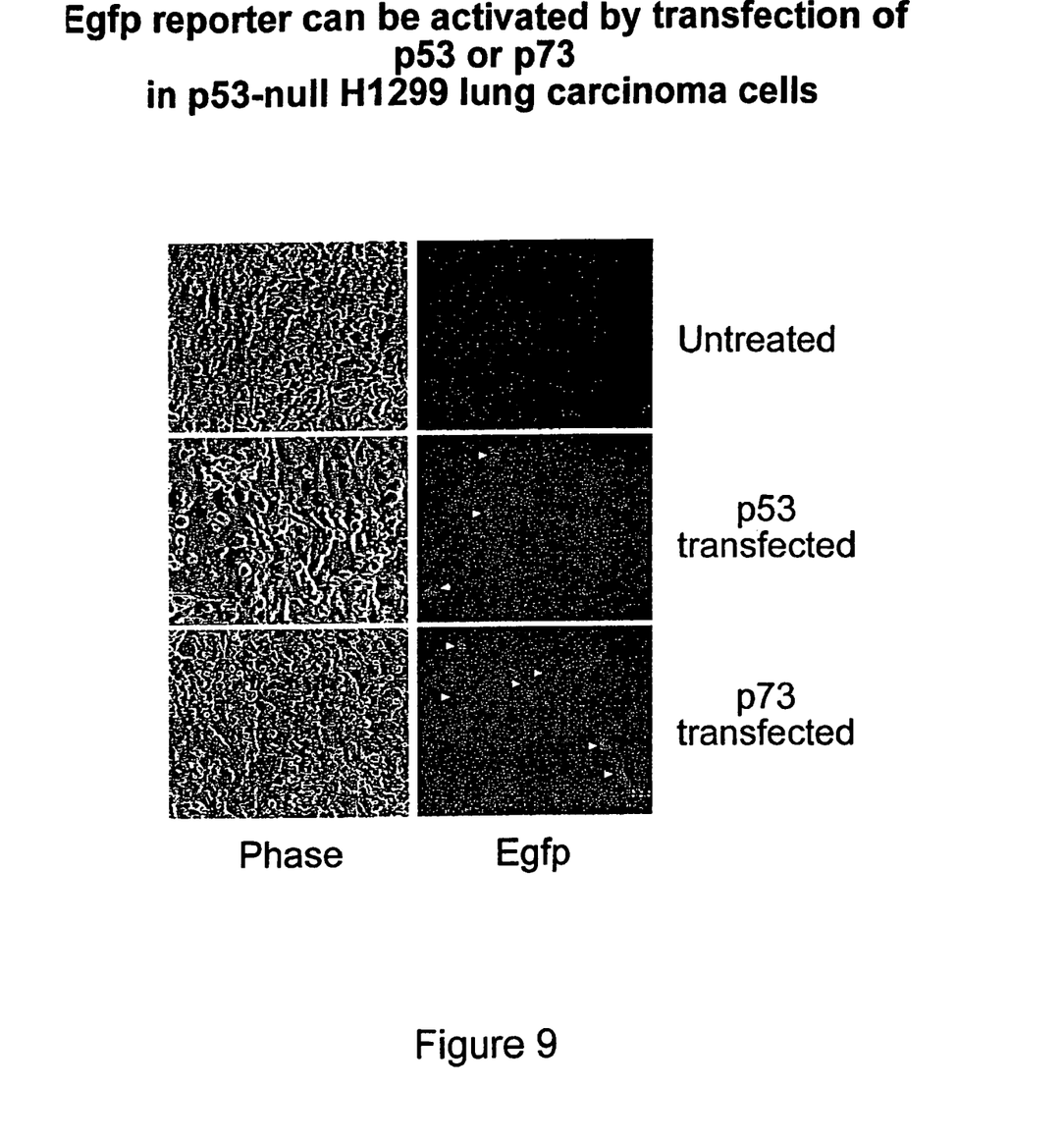
FIG. 9 shows results demonstrating that Egfp reporter can be activated by transfection of p53 or p73 in p53-null H1299 lung carcinoma cells.

In order to demonstrate that the screen works efficiently, the inventors have tested these cells using two independent methods. In the first, the cells were transfected independently with 3 different plasmids encoding beta-galactosidase gene, the p53 gene and the p73-beta gene. Transfected cells were monitored for expression of the Egfp protein and hence fluorescence under the fluorescence microscope. As depicted in FIG. 9, transfection of an irrelevant beta-galactosidase gene did not activate the Egfp gene. In contrast, transfection of either p53 or p73 resulted in induction of Egfp, and hence, the cells were green (as depicted by the arrow-heads). These results demonstrate that the reporter system works when the inducing genes are "exogenously" provided by transfection.

Figure 10:
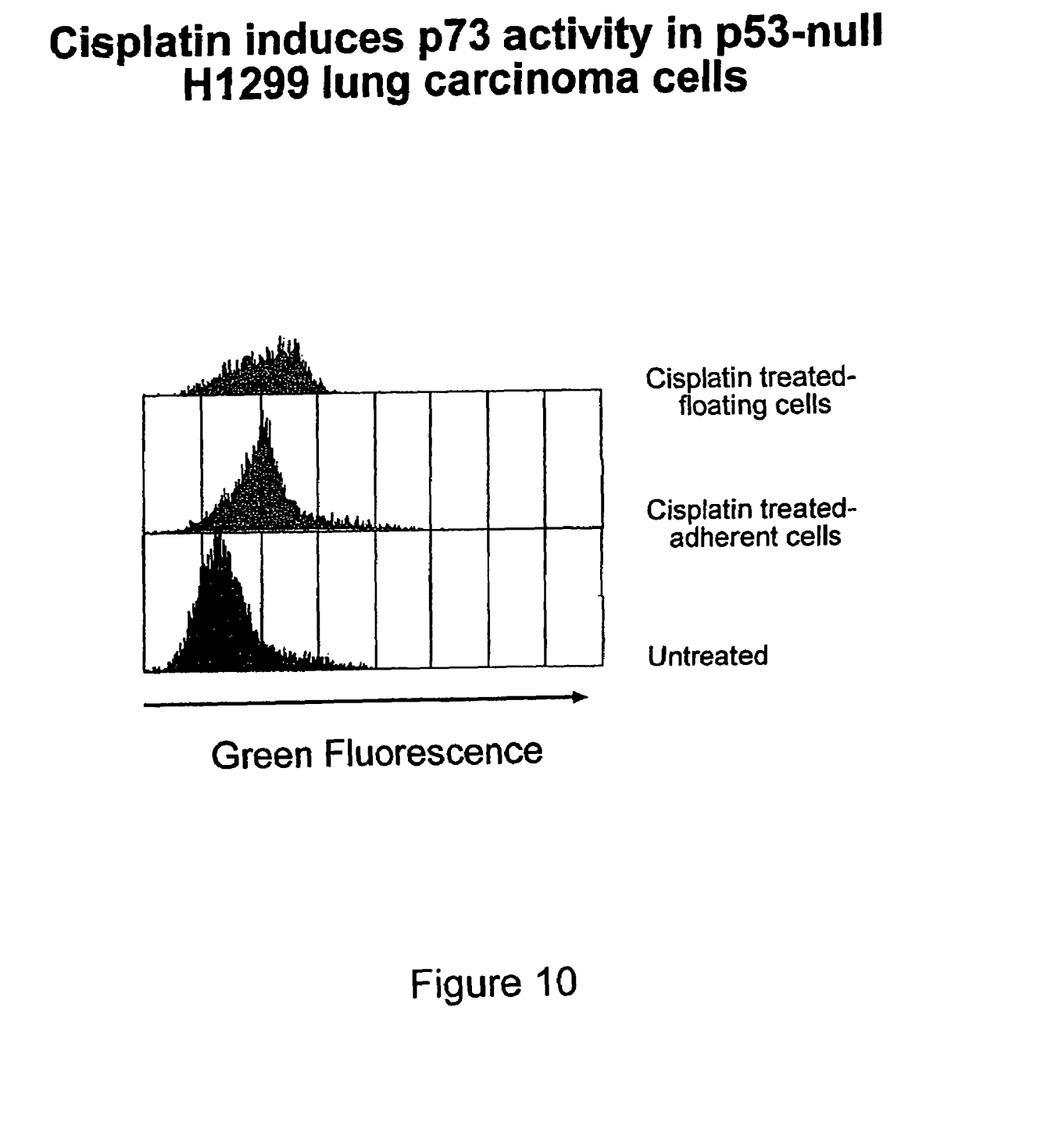
FIG. 10 shows results indicating that cisplatin induces endogenous p73 activity in p53-null H1299 lung carcinoma cells.

In order to demonstrate that the endogenous p73 activity in these cells can be activated (as p53 is not there in these cells), the inventors treated these cells with cisplatin, which has been demonstrated to induce endogenous p73 activity. Cisplatin treatment resulted in the expression of Egfp in all the cells, as analysed using the flow cytometer (FIG. 10). Cisplatin treated adherent cells and floating cells (which are dying) showed a clear shift in fluorescence compared to the untreated cells (FIG. 10), demonstrating that endogenous p73 activity can be activated in these cells and this activation can be visualised by both flow cytometric and microscopic methods. It is important to note that all the cells in the population expressed Egfp, implying that the cell-system generated is homogenous and results in a 100% response.

Thus, these cells could be used for large scale screening for activating compounds in 96/384 well micro-titre plates. Positive hits would be visualised under the fluorescence-ELISA plate reader over time intervals. Using this screening method, no fixation of the cells is required and the p73 activity can be monitored over time.

The screen takes advantage of "spotting" compounds that would functionally activate p73, and hence, would be useful to eradicate the growth of cancer cells. The positive hits may include novel compounds that would activate p73 through mechanisms that are not elucidated, or compounds that would mimic (mimetics) of c-Jun or c-Abl. Positive hits may be further characterised for toxicity and effects of tumour-growth inhibition in animal studies. Further, the compounds may be prepared into medicaments for the treatment of cancers.

The invention claimed is:

1. A method of screening for substances that are capable of mimicking the activity of c-Jun in stabilizing or activating p73, said method comprising:
   a) contacting a first reaction medium comprising a c-Jun$^{-/-}$ cell capable of expressing p73 said cell comprising a nucleic acid construct comprising a p73 binding site linked to a reporter gene,
   b) determining and comparing reporter gene expression level in a comparable second reaction medium untreated with the test substance, a test substances which alters reporter gene expression levels in the cells of step a) compared to the cells in step b) being identified as a stabilizer or activator of p73.

2. A method according to claim 1 wherein stabilizing or activating p73 comprises:
   i) increasing the halflife of p73;
   ii) potentiating p73 transcriptional activity;
   iii) activating p73 to induce cell cycle arrest; and/or
   iv) activating p73 mediated apoptosis.

3. A method according to claim 1 wherein the cell is also JNK$^{-/-}$.

4. A method according to claim 3 wherein the cell is JNK1$^{-/-}$ and JNK2$^{-/-}$.

5. A method according to claim 1 wherein the reporter gene is luciferase gene or green fluorescent protein gene.

6. A method according to claim 1 comprising a further step of preparing a pharmaceutical composition comprising the test substance.

7. A method according to claim 3 wherein the reporter gene is luciferase gene or green fluorescent protein gene.

8. A method according to claim 4 wherein the reporter gene is luciferase gene or green fluorescent protein gene.

9. A method according to claim 1 comprising a further step of preparing a pharmaceutical composition comprising the test substance.

10. A method according to claim 3 comprising a further step of preparing a pharmaceutical composition comprising the test substance.

11. A method according to claim 4 comprising a further step of preparing a pharmaceutical composition comprising the test substance.

* * * * *